(12) United States Patent
Chambers et al.

(10) Patent No.: US 6,225,511 B1
(45) Date of Patent: May 1, 2001

(54) SYNTHESIS OF FLUORINATED ETHERS

(75) Inventors: Owen Ross Chambers, Filton; Roderic Nigel Fraser Simpson, Tidenham Chase, both of (GB)

(73) Assignee: Rhone-Poulenc Chemicals Ltd., Hertfordshire (GB)

( * ) Notice: Subject to any disclaimer, the term of this patent is extended or adjusted under 35 U.S.C. 154(b) by 0 days.

(21) Appl. No.: 09/525,109

(22) Filed: Mar. 14, 2000

Related U.S. Application Data

(62) Division of application No. 08/150,268, filed on Nov. 10, 1993, now Pat. No. 6,054,626, which is a continuation of application No. 08/033,434, filed on Mar. 18, 1993, now abandoned, which is a continuation of application No. 07/782,323, filed on Oct. 24, 1991, now abandoned.

(30) Foreign Application Priority Data

Oct. 26, 1990 (GB) .................................................. 9023370

(51) Int. Cl.$^7$ .................................................... C07C 43/12
(52) U.S. Cl. ............................................................ 568/683
(58) Field of Search ............................................. 568/683

(56) References Cited

U.S. PATENT DOCUMENTS 2,614,129 11/1952 McBee et al. .
3,897,502 7/1975 Russell et al. .................... 260/614 F

FOREIGN PATENT DOCUMENTS 0 341 005   11/1989  (EP) .
WO 84/02909  7/1984  (WO) .

*Primary Examiner*—Jane C. Oswecki
(74) *Attorney, Agent, or Firm*—Finnegan, Henderson, Farabow, Garrett, & Dunner, L.L.P.

(57) ABSTRACT

Fluorinated ethers of the formula:

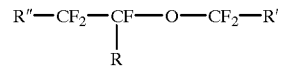

wherein R is hydrogen, fluorine, alkyl of 1 to 6 carbon atoms, or fluoroalkyl of 1 to 6 carbon atoms, R' is hydrogen, alkyl of 1 to 6 carbon atoms, or fluoroalkyl of 1 to 6 carbon atoms, and R" is fluorine, alkyl of 1 to 6 carbon atoms or fluoroalkyl of 1 to 6 carbon atoms are prepared by fluorinating a corresponding ether of formula:

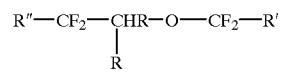

with a solid transition metal fluoride fluorinating agent such as cobaltic fluoride.

2 Claims, No Drawings

SYNTHESIS OF FLUORINATED ETHERS

This is a division of application Ser. No. 08/150,268, filed Nov. 10, 1993, now U.S. Pat. No. 6,054,626, which is a continuation of application Ser. No. 08/033,434, filed Mar. 18,1993, now abandoned, which is a continuation of application Ser. No. 07/782,323, filed Oct. 24, 1991, now abandoned, all of which are incorporated herein by reference.

This invention relates to the preparation of fluorinated ethers, and, especially, 2-difluoromethoxy-1,1,1,2-tetrafluoroethane, of formula: $CF_3CHFOCHF_2$.

This compound, called Desflurane, is known to have valuable anaesthetic properties—see, for example, E. I. Eger et al, Anaesthesia and Analgesia 1987, Volume 66 (10), pp. 971–973, 974–976, 977–982, 983–985, 1227–1229, 1230–1233, and 1312–1315.

This compound is mentioned in U.S. Pat. No. 3,897,502 (Example XXI; column 8, Table 1) and at column 1, line 23 ff, where it is stated that "polyfluoro containing products which can be made by the method of this invention are also useful as agents for producing anaesthesia in anaesthetic-susceptible, air breathing mammals".

The process disclosed in U.S. Pat. No. 3,897,502 for the production of this compound involves the direct fluorination of 2-difluoromethoxy-1,1,1-trifluoroethane. The reaction, which took 13 hours to complete, was conducted in the solvent Freon E3, using a mixture of 20% fluorine gas in argon, at −20° to −25° C. to control the exothermic process.

This process is obviously difficult to develop to a commercial scale, since expensive reagents are used, and the reaction has to be carried out at low temperature and is slow. Further, it is known to those skilled in the art that the interaction of fluorine gas and partially fluorinated hydrocarbon compounds is liable to cause explosions.

Other published routes to 2-difluoromethoxy-1,1,1,2-tetrafluoroethane involve (a) reaction of $CHCl_2OCH_2COCl$ or $CHCl_2OCHClCOCl$ (or a mixture of the two) with sulphur tetrafluoride (U.S. Pat. No. 4,855,511). This is a multistage process, using the highly toxic gaseous reagent sulphur tetrafluoride, which must be handled under pressure. There are likely to be significant handling problems on scale-up.

(b) reaction of $CF_3CHClOCF_2H$ with potassium fluoride. This can be carried out in the absence of solvent at 278° C. under a pressure of 500 p.s.i. (3450 kPa) in an autoclave, (U.S. Pat. No. 4,874,901) or in the presence of an aprotic solvent (sulpholane) with a phase transfer catalyst (tetramethyl ammonium chloride) at 210° C., again under pressure (UK Patent Specification No. 2,219,292). Since these processes have to be operated under pressure, they suffer from the disadvantage of high capital cost, and problems in scale-up—especially from the corrosive nature of the reagents. They are essentially batch processes.

(c) reaction of $CF_3CHClOCF_2H$ with bromine trifluoride at ambient temperature (European Patent Specification No. 341,004). Although this process gives a good yield (87%) in a short time, the reagent, bromine trifluoride, which is prepared from bromine and fluorine, is highly toxic and difficult to handle, leading to problems in scale-up to commercial quantities.

Accordingly, there is need for a process which can be used on an industrial scale without significant problems. It has now been found that certain fluorinated aliphatic ethers, including Desflurane, can be produced from corresponding less fluorinated ethers by contacting the latter in the vapour phase with a solid transition metal fluoride fluorinating agent.

The present invention accordingly provides a process for the preparation of a fluorinated ether of the formula

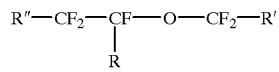

wherein R is hydrogen, fluorine, alkyl of 1 to 6 carbon atoms or fluoroalkyl of 1 to 6 carbon atoms, R' is hydrogen, alkyl of 1 to 6 carbon atoms, or fluoroalkyl of 1 to 6 carbon atoms, and R" is fluorine, alkyl of 1 to 6 carbon atoms or fluoroalkyl of 1 to 6 carbon atoms, which comprises reacting an ether of the formula:

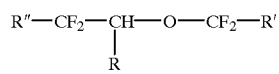

where R, R' and R" are as hereinbefore defined in the vapour phase with a solid transition metal fluoride fluorinating agent. The aforesaid fluoroalkyl groups are preferably perfluoroalkyl groups.

In the preferred operation of the process R is hydrogen or fluorine, especially hydrogen, R' is hydrogen or 1,2,2,2-tetrafluoroethyl, especially hydrogen and R" is fluorine.

Using the new process, the relatively easily available compound 2-difluoromethoxy-1,1,1-trifluoroethane ($CF_3CH_2OCHF_2$) can be fluorinated under relatively mild conditions in the vapour phase to 2-difluoromethoxy-1,1,1,2-tetrafluoroethane, i.e. Desflurane, using preferably cobalt trifluoride as the fluorinating agent. Difluoromethoxy-1,1,1,2,2-pentafluoro-ethane is produced at the same time.

Although cobalt trifluoride (cobaltic fluoride) is the preferred fluorinating reagent, other transition metal fluorides, which may be in the form of their alkali metal complexes, effective in replacing a hydrogen atom attached to carbon by fluorine may be used, e.g. silver difluoride, potassium tetrafluorocobaltate ($KCoF_4$), potassium hexafluoronickelate ($K_2NiF_6$), manganese trifluoride, cerium tetrafluoride, mercuric fluoride and potassium tetrafluoroargentate ($KAgF_4$). For simplicity the following discussion refers to cobalt trifluoride which is preferred.

Advantageously, in the operation of the new process, the transition metal fluoride fluorinating agent can be regenerated in situ during the reaction by passing fluorine into the reaction zone so that the cobalt trifluoride acts as a fluorine carrier. The following reactions, for example, then take place simultaneously:

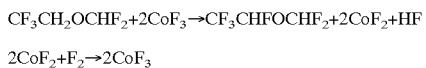

$2CoF_2 + F_2 \rightarrow 2CoF_3$

A cobalt trifluoride-based process is used commercially for the production of saturated fluorocarbons as described in, e.g., Preparation, Properties, and Industrial Applications of Organofluorine Compounds ed. R E Banks, published by Ellis Horwood/Wiley, 1982, p, 47) and the apparatus described therein may easily be used for the process of the present invention. The process of the present invention therefore provides a safe and economic route to 2-difluoromethoxy-1,1,1,2-tetrafluoroethane, which can easily be developed to commercial scale.

Since the trifluoroethane starting material has a boiling point of 29.2° C., simple heating will vaporise it. The fluorination will, in general, be carried out by contacting the ether starting material with cobalt trifluoride at a temperature of 100° to 450° C., preferably 150° C. to 300° C. and especially about 220° C. at atmospheric pressure. The cobalt trifluoride will normally be in a significant excess. This can be achieved quite simply by passing the ether starting material as a vapour through a bed of cobalt trifluoride, generally agitated, for example by stirring.

In one preferred embodiment of the invention, the starting material and the fluorine are continuously introduced into the reaction vessel, and the respective rates of introduction of these reagents are controlled so that the proportion of the cobalt (or other metal) in the form of the active fluorinating agent (e.g. $CoF_3$) is from 10% to 100% of the total cobalt or other metal, usually 10% to 80% and especially 33 to 67%.

While the starting material is preferably introduced as a vapour it can also be introduced in liquid form. If desired it may be mixed with a carrier gas, e.g. to facilitate temperature control, but this can reduce productivity.

The 2-difluoromethoxy-1,1,1-trifluoroethane starting material for the production of Desflurane can be obtained by known methods, for example by reacting trifluoroethanol with monochlorodifluoromethane under alkaline conditions (see, for example, UK Patent No. 1358960).

Purification of the crude product to the required quality can be achieved by the usual techniques of fractional distillation, using a column equipped with a high efficiency packing. Desflurane of high purity (>99.97%) can be obtained by a simple distillation. The level of impurities (other than unchanged starting material) is less than 30 ppm each.

The following Examples illustrate the present invention.

EXAMPLE 1

Preparation of 2-difluoromethoxy-1,1,1,2-tetrafluoroethane

2-Difluoromethoxy-1,1,1-trifluoroethane (FEFME) ($CF_3CH_2OCHF_2$) (50.0 g., 0.33 m) was passed through a stirred bed of cobalt trifluoride (10.0 kg, 86.3 m) held at a temperature of 220° C. The volatile product mixture was condensed in a trap held at −79° C. After washing with ice cold water, 35.0 g. of crude product were collected.

Analysis of this material by gas chromatography linked to mass spectrometry showed that it had the following composition: $CF_3CF_2OCF_3$ 8.8%; $CF_3CF_2OCHF_2$ 28.8%; $CF_3CH_2OCF_3$ 3.0%; $CF_3CHFOCHF_2$ 54.8%; $CF_3CH_2OCHF_2$ 4.6%. Thus the reaction yield of the target compound, 2-difluoro-methoxy-1,1,1,2-tetrafluoroethane ($CF_3CHFOCHF_2$) was 34.3%.

Fractional distillation in a laboratory still equipped with a high efficiency fractionating column gave the target compound Desflurane in excellent yield. The pure compound was unambiguously identified by comparison of its proton and $^{19}F$ n.m.r. spectra with that published in European Specification No. 341,004.

EXAMPLE 2

Preparation of 2-difluoromethoxy-1,1,1,2-tetrafluoroethane

2-Difluoromethoxy-1,1,1-trifluoroethane (FEFME) was passed into a stirred bed of cobalt difluoride/cobalt trifluoride mixture with a separate fluorine feed, over a period of 32.5 hours. The fluorine was produced by electrolysis. The reaction products were scrubbed with water to remove acidic components, and then condensed by compression and cooling.

Details of the run to produce crude Desflurane are given in Tables 1 and 2 below.

TABLE 1

Summary of Reaction Conditions for Desflurane Run

| | |
|---|---|
| Total FEFME ($CF_2CH_2OCF_2H$) feed | 103 kg (0.69 kg moles) |
| FEFME range of feed rates | 2–4 kg/hr |
| Total Fluorine feed | 22–25 kA hrs. ≡ ~8 × $10^7$ coulombs ≡ ~16 kg (0.4 kg moles)* |
| $F_2$ feed rate | 0.5–1 kA per hour |
| Average $F_2$:FEFME feed ratio (molar) | 0.6:1 |
| No. of hours running | ca. 30 hrs. |
| Reactor Temperature Range | 240–300° C. |
| $CoF_2$ charge | 180–200 kg |
| $CoF_2/CoF_3$ ratio range | controlled between 0.2 and 0.8 |
| Total crude product recovered | ~85 kg |

*Based on 1 Faraday = 96500 coulombs and 2 Faraday required for each mole $F_2$. Assumes 100% efficiency.

TABLE 2

Summary of Overall Reaction Yields, Selectivity and Mass Balance for the Desflurane Run

| 1. Reaction Yields | |
|---|---|
| $CF_3CF_2OCF_3$ | 0.06% |
| $CF_3CF_2OCHF_2$ | 2.6% |
| $CF_3CHFOCF_3$ | 0.7% |
| $CF_3CH_2OCF_3$ | 2.2% |
| $CF_3CH_2OCHF_2$ (unchanged FEFME) | 32.7% |
| $CF_3CHFOCHF_2$ (Desflurane) | 38.4% |
| 2. Organic balance | 77% |
| 3. Conversion of FEFME | 67% |
| 4. Selectivity to Desflurane | 57% |

EXAMPLE 3

Laboratory Distillation of Crude Desflurane

A two stage laboratory distillation of crude Desflurane (obtained as described above) was carried out to determine if it was possible to obtain Desflurane of anaesthetic quality. The initial distillation was carried out to remove the bulk of the low boilers. The Desflurane was then distilled off up a larger column.

Crude Desflurane (6.361 kg) was charged to a 5 L round bottomed flask and distilled up a 32"×1" (81 cm×1.3 cm) column packed with 1/16"×1/16" (1.6 mm×1.6 mm stainless steel Dixon gauzes. The condenser was run with chilled glycol (ca. −10° C.).

The upgraded Desflurane was then distilled up a 59"×1" (1.5 m×2.5 cm) column packed with 4"×1" (10 cm×2.5 cm) Knitmesh (RTM) sections. A swinging bucket take off head and a vertical condenser system were used, vented through a cold trap system. The average distillation offtake rate was ca. 4 g./hr. and the average reflux ratio was ca. 170:1.

According to the gas chromatography results obtained, two later fractions (84.9 g.) gave material with total impurities <0.05%. The best sample (11.5 g.), according to the analytical procedure, had a total impurity content of 0.03%.

EXAMPLE 4

Preparation of Hexafluoropropyl trifluoroethyl ether ($CF_3CHFCF_2OCH_2CF_3$:HFPTFE)

A 1 liter 3-necked flask was fitted with a mechanical stirrer, a fritted glass inlet, a thermocouple, and a reflux condenser (using a Swan neck adaptor).

The reactor was charged with trifluoroethanol (188.9 g., 1.89 moles) and potassium hydroxide (12.1 g., ca. 0.19 m). The mixture was cooled to 20° C. by an ice/salt bath and then held at this temperature during the hexafluoropropene (HFP) feed.

The HFP feed was introduced at 150 ml.min$^{-1}$ for 3 hours (total HFP introduced, ca. 1.102 m).

After the addition was complete, the product was water washed to give a clear liquid (250.3 g.) which was submitted for gc analysis. From this analysis the following product yields were calculated:.

|  | vs Trifluoro ethanol input | vs hexafluoro propene input |
| --- | --- | --- |
| Hexafluoropropene: recovery % | — | 12.3 |
| Pentafluoroallyl trifluoro ethyl ether: yield % | 0.3 | 0.5 |
| Hexafluoropropyl trifluoro ethyl ether: yield % | 41.7 | 71.6 |
| 2-Trifluoromethyl-1,2-difluoro-vinyl-2',2',2'-trifluoro ethyl ether (1): yield % | 1.3 | 2.3 |
| 2-Trifluoromethyl-1,2-difluoro-vinyl-2',2',2'-trifluoro ethyl ether (11): yield % | 6.2 | 10.7 |

Since the double bonds in the allyl and vinyl ethers are saturated with fluorine by reaction with cobalt fluoride, the combined crudes were submitted for fluorination over cobalt trifluoride.

Fluorination of Crude HFPTFE

The crude product from the addition of hexafluoropropene to trifluoroethanol as described above (142 g.) was volatilised into a horizontal stirred reactor containing cobalt trifluoride at 220° C. The product was collected in traps cooled to −78° C., and on working up a fluorinated mixture (100 g.) was obtained.

This crude fluorinated material was shown by gas chromatography linked mass spectrometry to have the following composition:

|  | % by wt. | References | B.Pt. ° C. |
| --- | --- | --- | --- |
| $CF_3CF_2CF_2OCF_2CF_3$ | 0.8 | 2, 3(b) |  |
| $CF_3CF_2CF_2OCHFCF_3$ | 5.2 | 3(a) |  |
| $CF_3CHFCF_2OCF_2CF_3$ | 18.3 | * | 40–45 |
| $CF_3CF_2CF_2OCH_2CF_3$ | 1.5 | * |  |
| $CF_3CHFCF_2OCHFCF_3$ | 61.0 | * | 54 |
| $CF_3CHFCF_2OCH_2CF_3$ | 13.2 | 1 | 74 |

\* New Compound
1 V A Gubanov, A V Tumanova and I M Dolgopol'skii Zh. Obshch. Khim, 1965 35 (2) 389–400
2 U.S. 4,523,039 (1985)
3(a) EP 260,773 (1988)
3(b) Japan Kokai 78 21,112

This mixture was fractionally distilled at atmospheric pressure up a column, and a fraction, b.p. 52–56° C., containing 93.3% by wt. of 2-H-hexafluoropropyl-1'H-tetrafluoroethyl ether and 6.0% of 2-H-hexafluoropropyl-2', 2',2'-trifluoroethyl ether was obtained.

The $^{19}F$ nmr spectra of the components of the product were consistent with the proposed structures.

We claim:

1. A compound selected from the group consisting of 2H-hexafluoropropyl-1'H-tetrafluoroethyl ether, 2H-hexafluoropropyl-pentafluoroethyl ether, and heptafluoropropyl-2'2'2'-trifluoroethyl ether.

2. A fluorinated ether product prepared by a process comprising a reacting fluorinated ether of the formula:

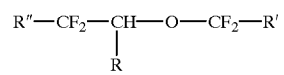

wherein R is hydrogen, R' is hydrogen or —CHFCF$_3$, and R" is fluorine or perfluoroalkyl of 1 to 6 carbon atoms in the vapor phase with a solid transition metal fluoride fluorinating agent selected from the group consisting of cobalt trifluoride, silver difluoride, potassium tetrafluorocobaltate, potassium hexafluoronickelate, manganese trifluoride, cerium tetrafluoride, mercuric fluoride and potassium tetrafluoroargentate.

\* \* \* \* \*